(12) United States Patent
Hollander

(10) Patent No.: US 6,614,039 B2
(45) Date of Patent: *Sep. 2, 2003

(54) HERMETICALLY SEALED ULTRAVIOLET LIGHT SOURCE

(76) Inventor: Brad C. Hollander, P.O. Box 1270, Minden, NV (US) 89423

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/339,027
(22) Filed: Jun. 23, 1999

(65) Prior Publication Data
US 2003/0001112 A1 Jan. 2, 2003

(51) Int. Cl.$^7$ ................................................. H01J 61/40
(52) U.S. Cl. .............................. 250/504 R; 250/493.1; 250/494.1; 313/489; 313/112
(58) Field of Search .......................... 250/458.1, 468.1, 250/504 R, 461.1; 313/489, 493, 25, 634

(56) References Cited

U.S. PATENT DOCUMENTS

| | | | |
|---|---|---|---|
| 2,382,939 A | 8/1945 | Koch | 240/11.4 |
| 3,179,792 A | 4/1965 | Weiss | 240/11.4 |
| 3,563,241 A | 2/1971 | Evans | |
| 3,899,392 A | 8/1975 | Grossman et al. | 176/68 |
| 3,936,246 A | 2/1976 | Beitzel | |
| 3,979,633 A | 9/1976 | Davis et al. | 313/481 |
| 3,996,474 A | 12/1976 | Lowther | |
| 4,048,537 A * | 9/1977 | Blaisdell et al. | 313/489 |
| 4,071,335 A | 1/1978 | Barosi | 55/68 |
| 4,077,899 A | 3/1978 | van Gils | 252/181.4 |
| 4,100,415 A | 7/1978 | Blaisdell et al. | |
| 4,112,485 A | 9/1978 | Sutter | 362/369 |
| 4,127,361 A | 11/1978 | Hellier et al. | 417/48 |
| 4,141,830 A | 2/1979 | Last | 210/63 Z |

(List continued on next page.)

FOREIGN PATENT DOCUMENTS

WO WO99/58453 11/1999

OTHER PUBLICATIONS

Light Sources, Inc. Product Innovations for the '90's; Germipak™ UV Cells Integral Germicidal Lamps and Sleeves, p. 25.

(List continued on next page.)

Primary Examiner—John R. Lee
Assistant Examiner—David A. Vanore
(74) Attorney, Agent, or Firm—Townsend and Townsend and Crew, LLP

(57) ABSTRACT

An ultraviolet light source which includes an ultraviolet light bulb or lamp, a power source for providing power to the ultraviolet light bulb, and a non-glass or non-quartz protective sleeve which surrounds the ultraviolet light bulb. The ultraviolet light bulb preferably includes a casing for holding a starting gas and a vaporizable material, and at least one electrode electrically coupled to the power source for exciting the starting gas and the vaporizable material within the casing. The casing is made of soft glass or quartz material, and the protective sleeve is a fluoropolymer sleeve which surrounds the soft glass or quartz casing. The fluoropolymer sleeve may comprise any suitable fluoropolymer material, such as Teflon® products like PTFE, FEP, PFA, AF, Tefzel® ETFE, and the like. In addition, some silicon based materials or other UV transmissive non-glass materials can be used for the protective sleeve.

32 Claims, 7 Drawing Sheets

U.S. PATENT DOCUMENTS

| | | | |
|---|---|---|---|
| 4,306,887 A | 12/1981 | Barosi et al. | 55/68 |
| 4,342,662 A | 8/1982 | Kimura et al. | 252/181.4 |
| 4,762,613 A | 8/1988 | Snowball | |
| 4,804,886 A | 2/1989 | Nolan | 313/489 |
| 4,963,750 A | 10/1990 | Wilson | 250/436 |
| 4,968,489 A | 11/1990 | Peterson | 422/186.3 |
| 5,006,244 A | 4/1991 | Maarschalkerweerd | 210/243 |
| 5,043,626 A | 8/1991 | Nolan | 313/489 |
| 5,106,495 A | 4/1992 | Hughes | 210/139 |
| 5,118,988 A | 6/1992 | della Porta | 313/561 |
| 5,200,156 A | 4/1993 | Wedekamp | 422/186.3 |
| 5,320,749 A | 6/1994 | Mullen | |
| 5,322,569 A | 6/1994 | Titus et al. | |
| 5,334,347 A * | 8/1994 | Hollander | 422/22 |
| 5,372,781 A | 12/1994 | Hallett et al. | |
| 5,441,179 A | 8/1995 | Marsh | 222/190 |
| 5,451,790 A | 9/1995 | Enge | 250/436 |
| 5,451,791 A | 9/1995 | Mark | 250/438 |
| 5,471,063 A | 11/1995 | Hayes et al. | 250/436 |
| 5,493,124 A | 2/1996 | Shapiro | 250/373 |
| 5,503,800 A | 4/1996 | Free | 422/24 |
| 5,532,549 A | 7/1996 | Duzyk et al. | 313/489 |
| 5,587,069 A | 12/1996 | Downey, Jr. | |
| 5,614,151 A | 3/1997 | LeVay et al. | 422/24 |
| 5,635,059 A | 6/1997 | Johnson | |
| 5,690,057 A | 11/1997 | Curry | |
| 5,729,085 A * | 3/1998 | Sica et al. | 313/493 |
| 5,753,996 A | 5/1998 | Csoknyai | 313/318.05 |
| 5,780,860 A | 7/1998 | Gadgil et al. | |
| 5,792,433 A | 8/1998 | Kadoya | |
| 5,817,276 A | 10/1998 | Fencl et al. | 422/24 |
| 5,937,266 A | 8/1999 | Kadoya | |
| 6,007,781 A | 12/1999 | Campbell et al. | |
| 6,020,402 A | 2/2000 | Anand et al. | |
| 6,038,120 A | 3/2000 | May et al. | |
| 6,042,720 A | 3/2000 | Reber et al. | 210/85 |
| 6,090,281 A | 7/2000 | Buckner | |
| 6,117,335 A | 9/2000 | Bender | |
| 6,221,247 B1 | 4/2001 | Nemser et al. | |
| 6,245,183 B1 | 6/2001 | Iorio et al. | |

* cited by examiner

HERMETICALLY SEALED ULTRAVIOLET LIGHT SOURCE

CROSS-REFERENCES TO RELATED APPLICATIONS

This application was filed concurrently with: U.S. Pat. No. 6,193,894, which issued on Feb. 27, 2001 and is entitled "METHODS AND APPARATUS FOR DISINFECTING AND STERILIZING WATER IN WATER DISPENSERS USING ULTRAVIOLET RADIATION"; and U.S. patent application Ser. No. 09/339,057, entitled "METHODS AND APPARATUS FOR DISINFECTING AND STERILIZING FLUIDS USING ULTRAVIOLET RADIATION", both of which are incorporated herein by reference for all purposes.

BACKGROUND OF THE INVENTION

The present invention relates generally to methods and apparatus for disinfecting and sterilizing fluids using an ultraviolet light source, and more particularly to a novel ultraviolet lamp which can be used in a wide variety of harsh environments to kill micro organisms living in fluids.

The use of ultraviolet light sources for sterilizing and disinfecting fluids is well-known in the art. A typical ultraviolet light source has two primary parts, the tube and the base. The tube usually comprises a soft glass or quartz casing which holds a vaporizable material, such as mercury, and a starting gas and/or stabilizing gas, such as argon, neon, zeon or the like. The tube also includes one or more electrodes, which when provided with power, excite the gas and the vaporizable material. The excited vaporizable material causes a plasma field which generates the ultraviolet light.

In addition to the tube, an ultraviolet light source typically comprises a base, which is designed to hold the tube in place during operation, but which allows the tube to be removed and replaced when necessary.

While ultraviolet light sources have been used for some time for sterilization purposes, a problem with the ultraviolet light sources currently known in the art is that they are fragile and typically cannot handle the harsh environments in which they must be used. For example, because the prior art ultraviolet light sources are made of soft glass or quartz, the lamps tend to break easily. In addition, because of the adhesive nature of the soft glass or quartz casing, residue and other impurities tend to build up on the lamps over time, affecting the performance of the lamp. Finally, the prior art ultraviolet light sources have a tendency to be expensive and difficult to maintain. Therefore, what is needed is an inexpensive, impact resistant ultraviolet light source, which can be used for sterilization purposes, can be easily introduced into existing systems, is thermally stable in cold or hot fluids including air, and does not require significant modification of the system.

SUMMARY OF THE INVENTION

According to one embodiment of the invention, an ultraviolet light source which includes an ultraviolet light bulb or lamp, a power source for providing power to the ultraviolet light bulb, and a non-glass or non-quartz protective sleeve which surrounds the ultraviolet light bulb. The ultraviolet light bulb preferably includes a casing for holding a starting gas and a vaporizable material, and at least one electrode electrically coupled to the power source for exciting the starting gas and the vaporizable material within the casing. In accordance with one embodiment of the present invention, the casing is made of soft glass or quartz material, and the protective sleeve is a UV transparent or transmissive material. For example, the protective sleeve may comprise a fluoropolymer sleeve which surrounds the soft glass or quartz casing. The fluoropolymer sleeve may comprise any suitable fluoropolymer material, such as the Teflon® family of products like PTFE, FEP, PFA, AF, Tefzel® ETFE, and all other Teflon® products developed in the future. In addition, some silicone based materials, like silicone polymers, and other UV transmissive non-glass materials can be used for the protective sleeve.

In accordance with another embodiment of the present invention, instead of the casing being a quartz or soft glass casing surrounded by a fluoropolymer sleeve, the casing itself may be made of the fluoropolymer material. Thus, instead of two layers for the casing (i.e., the soft glass or quartz, and the fluoropolymer sleeve), a single layer fluoropolymer or other UVC transparent material casing can be used.

In accordance with yet another embodiment in the present invention, the protective sleeve may comprise a permanent sleeve surrounding the ultraviolet light source, or the protective sleeve may comprise a removable container, so that the ultraviolet light bulb can be replaced when it burns out or malfunctions. In the case where the protective sleeve is permanent, the sleeve may preferably comprise a fluoropolymer, silicone or other UV transmissive material which is heat shrunk around the ultraviolet light bulb or the entire light source, or the fluoropolymer, silicone or other UV transmissive material is applied by pressing it onto the light source, or dipping the light source into a liquid form of the material.

The protective sleeve seals in the soft glass or quartz casing, protecting it from breakage. However, in situations where the glass or quartz does break, the protective sleeve contains the glass particles and harmful mercury vapor material so that the environment in which the lamp is used is not exposed to the glass and mercury materials. Said another way, the protective sleeve hermetically seals the lamp. For example, if the lamp is used in a drinking water supply tank, and the glass or quartz casing of the lamp happens to break, the protective sleeve prevents the glass or quartz particles, as well as the harmful mercury within the lamp from contaminating the drinking water supply. In addition, the protective sleeve preferably acts as a thermal insulator, which helps keep the ultraviolet light's plasma thermally stable.

The ultraviolet light source of the present invention may be used for sterilizing and/or disinfecting fluids, as well as the surfaces of containers, pipes, ducts, or other suitable devices with which the fluid contacts. As one skilled in the art will appreciate, the term fluid includes air, water and other suitable fluids. The ultraviolet light which illuminates from the ultraviolet light source may comprise any suitable UV light, such as UVA, UVB, UVC, or the like. However, in accordance with one embodiment of the present invention, the light is a UVC light (e.g., light having a wavelength between about 180 nm and about 325 nm), which is good for killing living organisms, such as molds, bacteria, viruses, and the like. Because of the resilient nature of the protective sleeve of the present invention, the ultraviolet light source can be used in virtually any environment where it is beneficial to disinfect and/or sterilize a fluid.

A more complete understanding of the present invention may be derived by referring to the detailed description of preferred embodiments and claims when considered in connection with the figures, wherein like reference numbers refer to similar items throughout the figures.

DESCRIPTION OF THE SPECIFIC EMBODIMENTS

The present invention relates generally to methods and apparatus for disinfecting and sterilizing fluids and the surfaces of containers, pipes, ducts and other suitable devices with which the fluids contact. More particularly, the present invention relates to a novel embodiment of an ultraviolet light source, which performs the disinfecting and sterilizing processes.

In accordance with the present invention, the term fluid means a continuous, amorphous substance whose molecules move freely past one another and that has the tendency to assume the shape of its container; that is, a fluid can be a liquid or gas, including air. In addition, the term may refer to plasma type materials.

Figure 1:
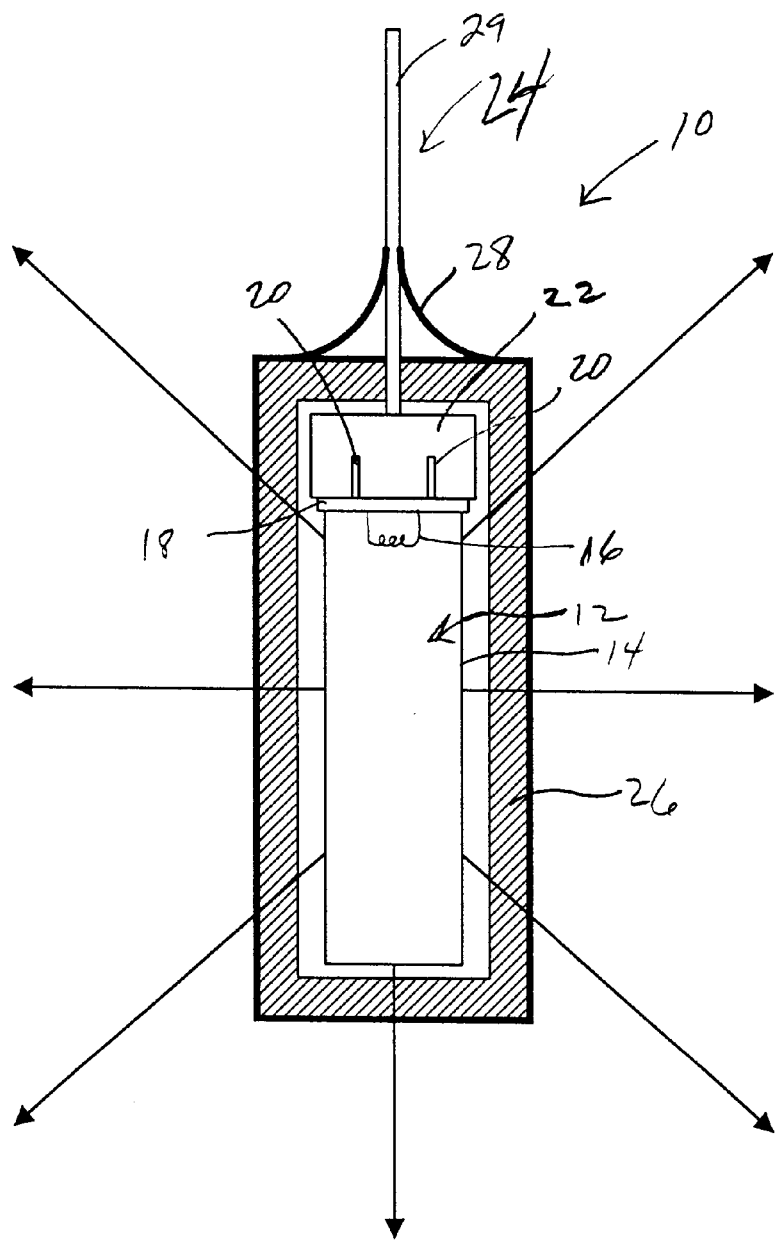
FIG. 1 is a side cross-sectional view of an ultraviolet light source having a protective sleeve.

Referring now to FIG. 1, an apparatus 10 for disinfecting and/or sterilizing a fluid is shown. In accordance with the illustrated embodiment, Apparatus 10 comprises an ultraviolet lamp or light bulb 12, a base 22, a power source 24, and a protective coating or sleeve 26.

Ultraviolet lamp 12 preferably comprises a soft glass or quartz tube 14, and at least one filament electrode 16 which preferably is mounted on an end seal 18. One or more base pins 20 are connected to end seal 18, and are adapted to insert into base 22 which, as discussed in more detail below, provides power to ultraviolet lamp 12 through end pins 20.

Glass tube 14 preferably is filled with one or more rare gases, such as argon, neon, xenon and/or krypton. In addition, a small amount of mercury or other suitable metal element is provided within glass tube 14. During operation of ultraviolet lamp 12, electrons are emitted from electrode 16, which is heated when power from base 22 is provided to lamp 12. The electrons are accelerated by the voltage across the tube until they collide with the mercury or other metal atoms, causing them to be ionized and excited. When the mercury or other metal atoms return to their normal state, spectral lines in both the visible and the ultraviolet regions are generated. The low and/or mid pressure within glass tube 14 enhances the ultraviolet radiation.

As one skilled in the art will appreciate, base 22 may include a ballast which is configured to provide a starting voltage and current for lamp 12, and limit the lamp current to the required value for proper operation. In addition, for rapid-start type lamps, the ballast can provide low-voltage cathode heating. The ballast may be a fixed-impedance type ballast, a variable-impedance type ballast or any other suitable electronic ballast currently known in the art. Preferably, electrical source 24 is configured to provide power to base 22 and the bulbs of which may be configured within the base. In addition, while the ballast may be configured within base 22, one skilled in the art will appreciate that the ballast may be separate from base 22, and power is provided from the ballast to base 22 via an electrical lead connection.

In accordance with a further aspect of the present invention, base 22 may comprise a metal, a ceramic material, a plastic material, or a material which allows UV light to pass, such as a fluoropolymer material, or a silicon polymer or silicone material.

Protective coating or sleeve 26 may comprise any suitable UV transmissive material. In accordance with one embodiment, sleeve 26 comprises a fluoropolymer material, which is transparent to ultraviolet light, such as the Teflon® family of products like PTFE, FEP, PFA, AF, Tefzel® ETFE. Alternatively, protective coating of sleeve 26 may comprise a suitable silicon polymer or silicone material, or sleeve 26 may comprise other UV transmissive materials. Protective sleeve 26, protects the soft glass or quartz tube 14 from high impact collisions. As one skilled in the art will appreciate, fluoropolymer and silicone coatings are resistant to impacts, and therefore will protect the glass tube. In addition, in situations in which the soft glass or quartz casing actually breaks from a high impact collision, protective sleeve 26 is adapted so that it contains the glass or quartz particles and harmful mercury material therein, preventing the glass and mercury from getting into the fluid in which the lamp is placed. That is, protective sleeve 26 hermetically seals lamp 12. Moreover, protective sleeve 26 acts as an insulating layer, keeping the temperature of the lamp and in particular the temperature of the plasma within tube 14 at a more stable, proper operating temperature. In accordance with this particular aspect of the present invention, the insulating protective sleeve can be a single sleeve or a double insulating sleeve. In either case, the single or dual layered sleeve acts as a thermal insulator.

Finally, because of the inert nature of the fluoropolymer sleeves, as well as other suitable UV transmissive sleeves, apparatus 10 can be placed in many environments that are not suitable for the quartz or soft glass lamps currently known in the art. For example, apparatus 10 having sleeve 26 can be used in medical environments or other industrial environments using caustic chemicals. That is, apparatus 10 can be used to disinfect or sterilize pharmaceutical materials or other materials having low and/or high pH levels, because sleeve 26 does not interact with these materials. Also, because the fluoropolymer materials and some other UV transmissive materials have inherent anti-adhesion properties, apparatus 10 can be placed in many fluids or fluid environments, such as sewage treatment facilities, or the like, without caustic or corrosive materials adhering to the sleeve. As one skilled in the art will appreciate, ultraviolet lamps which merely have a quartz or soft glass tube, often have problems with caustic or corrosive materials adhering to them.

Figure 2:
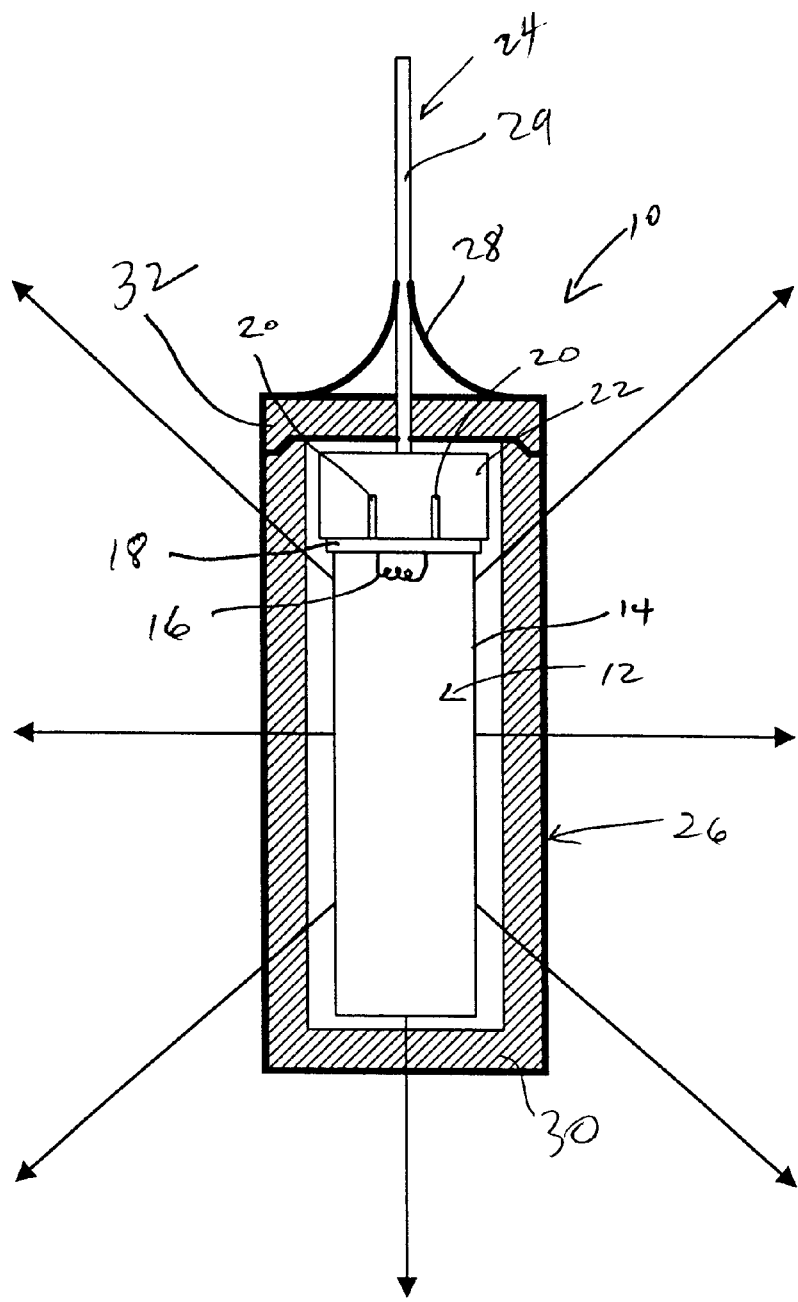
FIG. 2 is a side cross-sectional view of an ultraviolet light source having a protective sleeve with a removable cap.

As illustrated in FIG. 1, protective sleeve 26 may comprise a single piece of coating which surrounds ultraviolet lamp 12 and ballast 22. Coating 26 may be formed around lamp 12 and base 22 by any suitable molding technique known in the art. In addition, as illustrated in FIG. 2, coating 26 may be configured from multiple pieces. For example, as illustrated in FIG. 2, coating 26 preferably comprises a body portion 30 and a cap or lid portion 32. Lid portion 32 may be removably attached to body portion 30 so that one can readily access lamp 12. In accordance with this aspect of the invention, lamp 12 may be changed in the event of its failure or malfunction, or a different lamp 12, for example a lamp emitting different ultraviolet wave lengths, can be used in different fluid types.

Sleeve 26 may be any shape that is suitable for its intended application. For example, sleeve 26 may be cylindrical, spherical, square, or sleeve 26 may be a particular shape to fit into a specific location or to provide specific fluid dynamic characteristics when apparatus 10 is placed in a fluid containing device. Moreover, as discussed in more detail below, sleeve 26 may be shrink-wrapped or pressed onto ultraviolet lamp 12 and/or base 22, so that sleeve 26 takes on the shape of the lamp and base assembly. Alternatively, the ultraviolet lamp can be dipped into a liquid fluoropolymer material or other suitable UV transmissive containment material as discussed above in liquid form. Thus, when the lamp is removed, a film of the fluoropolymer or other material forms on and to the shape of the lamp assembly. As one skilled in the art will appreciate, the lamp assembly can take on any suitable shape or form.

Power source 24 preferably is connected in electrical communication with base 22 and comprises any suitable power source. For example, as illustrated in FIGS. 1 and 2, power source 24 may be an AC or DC power source located a distance from base 22 and lamp 14. In this manner, a suitable electrical connector 29 connects power source 24 with base 22. If power source 24 comprises a long electrical connector, connector 24 may be covered by a suitable insulating layer, or it may be covered by a fluoropolymer, silicone or other UV transmissive material such as that used for sleeve 26. In addition, a seal 28 may be provided around electrical connector 29 for preventing fluids and other materials from seeping through the interface between protective sleeve 26 and electrical connector 29. Seal 28 preferably comprises a flexible material so that it can relieve some of the stress put on electrical connector 29 by the movement of apparatus 10.

In accordance with an alternative embodiment of the present invention, power source 24 may be a battery pack or solar power generator connected directly to base 22. In accordance with this particular embodiment, sleeve 26 preferably covers both light source 12 and power source 24. In addition, if power source 24 comprises a battery pack or solar power generator connected directly to base 22, then base 22 preferably will include the ballast therein.

Figure 3:
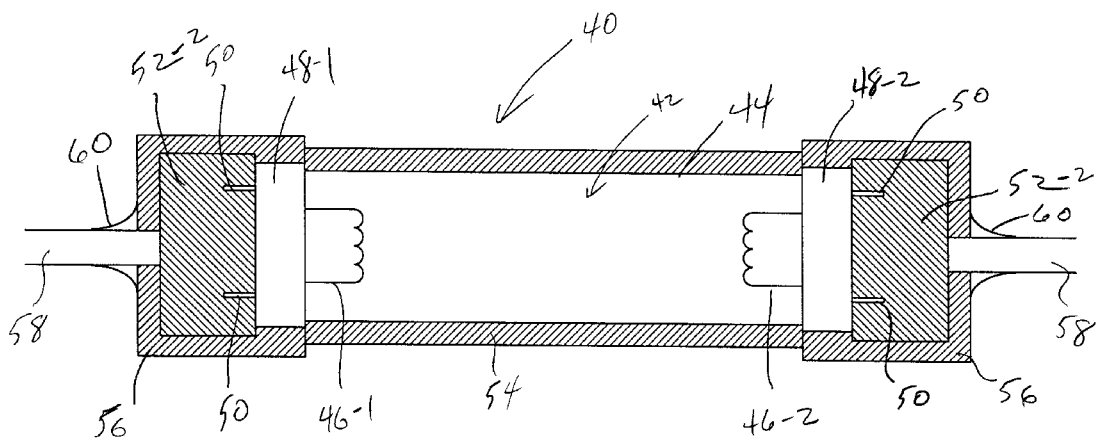
FIG. 3 is a side cross-sectional view of a first embodiment of an ultraviolet light source having a protective sleeve or coating surrounding the light source.

Referring now to FIG. 3, another embodiment of an ultraviolet light source 40 is illustrated. In accordance with this particular embodiment of the present invention, ultraviolet light source 40 preferably comprises an ultraviolet lamp 42 having a quartz or glass tube 44 and two electrodes 46-1 and 46-2 disposed at opposite ends of tube 44. As with the embodiments described above with reference to FIGS. 1 and 2, tube 44 preferably is lined with a phosphor material and it is filled with an inert gas and a metal element. Light source 40 further includes two end seals 48-1 and 48-2 disposed at both ends of tube 44. End seals 48-1 and 48-2 both include base pins 50 which electrically couple lamp 42 to a base 52, having a first end 52-1 and a second end 52-5. In accordance with the embodiment of the present invention illustrated in FIG. 3, tube 44 preferably is surrounded by a protective coating or sleeve 54, such as a fluoropolymer, silicone or other UV transmissive coating as discussed above. In addition, end seals 48 and base 52 preferably are covered by suitable end caps 56. Like protective coating 54, end caps 56 may comprise a fluoropolymer material, or end caps 56 may comprise a silicon polymer or silicone material or other suitable UV transmissive materials which can be used for this intended purpose. In any event, both protective sleeve 54 and end caps 56 preferably are transparent to the ultraviolet radiations emitting from ultraviolet light source 40. Preferably, lead wires 58 are configured to provide power to base 52, and seals 60 may be provided to seal the interface between end caps 56 and lead wires 58. In addition, as discussed above, base 52 may include a ballast, or the ballast may be separated from, but electrically coupled to base 52.

Protective coating 54 may comprise a rigid tube or container, or protective coating 54 may be a flexible fluoropolymer or silicone material which is heat shrunk around tube 44 of lamp 42. In addition, end caps 56 may be removable from lamp 42 and base 52, so that the lamp can be replaced when necessary, or end caps 56 may be securely bonded to protective coating 54, thus creating a fluid tight seal. As mentioned above, if the quartz or glass tube 44 of lamp 42 happens to break, it is preferable to securely contain the broken glass and caustic mercury material away from the fluid in which the lamp is being used. Preferably, a bonding glue or bonding material, such as RTV, or other silicone materials can be used to securely bond end caps 56 to protective coating 54.

Figure 4:
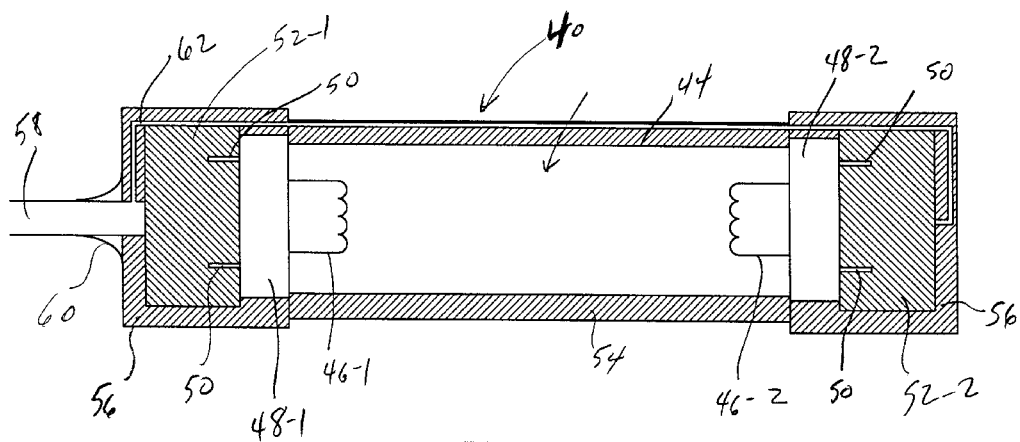
FIG. 4 is a side cross-sectional view of a second embodiment of an ultra light violet light source having a protective sleeve or coating surrounding the light source.

Referring now to FIG. 4, yet another embodiment of an ultraviolet light source 40 is illustrated. This particular embodiment of the present invention is similar to ultraviolet light source 40 of FIG. 3, except only one electrically lead wire 58 is provided. In this manner, a small electrical wire 62 runs from lead wire 58 to second base end 52-2, and provides power to the second base end 52-2.

Figure 5:
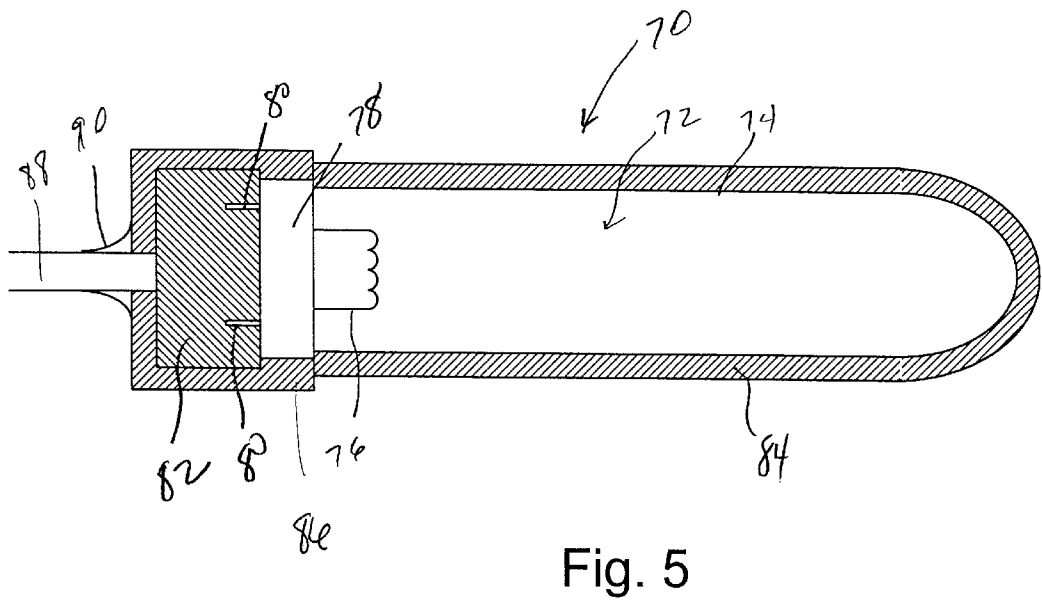
FIG. 5 is a side cross-sectional view of a third embodiment of an ultraviolet light source having a protective sleeve or coating surrounding the light source.

Referring now to FIG. 5, still another embodiment of an ultraviolet light source 70 is shown. In accordance with this particular embodiment of the present invention, ultraviolet light source 70 preferably comprises an ultraviolet lamp 72 having a quartz or glass tube 74 and an electrode 76. As with the other embodiments of the present invention, within glass tube 74 is a metal material, such as mercury, and one or more inert gases, such as argon, neon, xenon or krypton. In addition, at one end of lamp 72 is an end seal 78 having base pins 80, which provide electrical communication to a base 82. Preferably, an electrical lead wire 88 is used to provide power to base 82. As with the embodiments illustrated in FIGS. 3 and 4, tube 74 preferably is surrounded by a protective coating 84 which, as discussed above, preferably comprises a fluoropolymer or silicone material. In addition, an end cap 86 preferably covers base 82 and end seal portion 78 of lamp 72. As with the embodiments discussed above with reference to FIGS. 3 and 4, a seal 90 surrounds electrical lead 88 and prevents fluid from entering between lead 88 and end cap 86. Also, as discussed above, end cap 86 can be removable, or securely bonded to protective coating 84.

Figure 6:
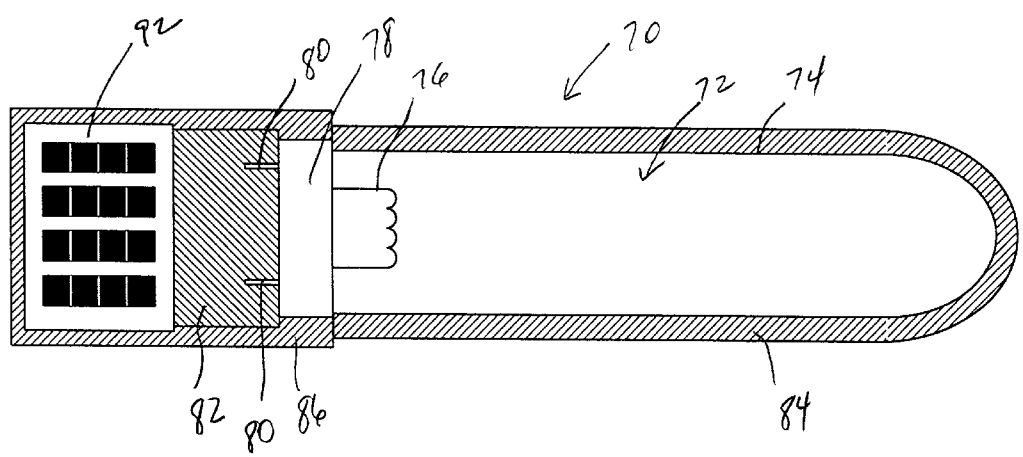
FIG. 6 is a side cross-sectional view of a fourth embodiment of an ultraviolet light source having a protective sleeve or coating surrounding the light source.

Referring now to FIG. 6 another embodiment of ultraviolet light source 70 is illustrated. The embodiment in FIG. 6 is similar to the embodiment of FIG. 5 except that instead of an electrical lead 88 providing power to base 82, a solar power generator 92 provides the power. In accordance with this particular embodiment of the present invention, end cap 86 is configured to cover end seal 78, base 82, and solar power generator 92. In addition, while the embodiment illustrated in FIG. 6 shows a solar power source providing power to base 82, a battery pack or other suitable power source can be used in a similar manner.

Figure 7:
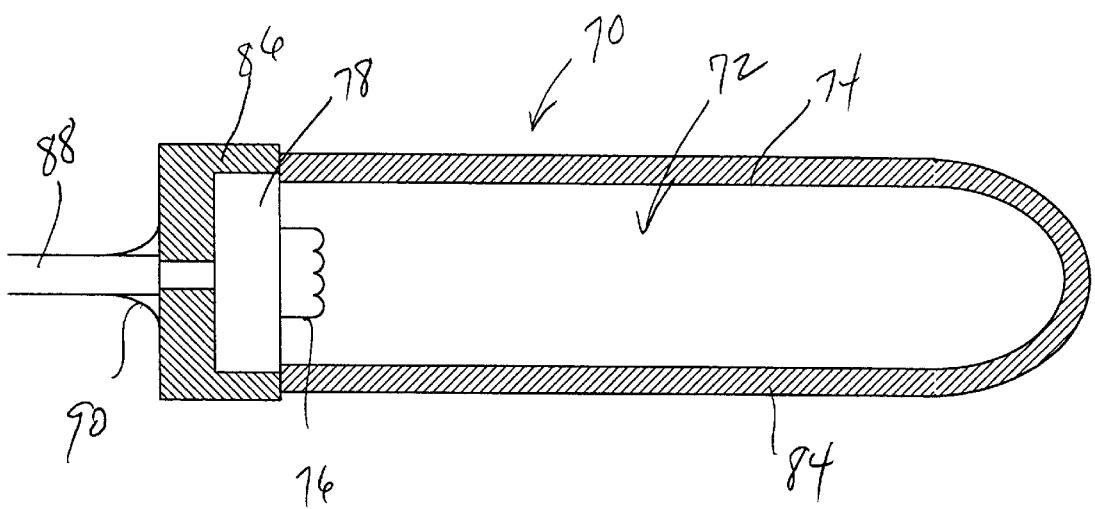
FIG. 7 is a side cross-sectional view of a fifth embodiment of an ultraviolet light source having a protective sleeve or coating surrounding the light source.

Referring now to FIG. 7, yet another embodiment of ultraviolet light source 70 is shown. In accordance with this particular embodiment of the present invention, ultraviolet light source 70 preferably comprises an ultraviolet lamp 72 having a glass or quartz tube 74, an electrode 76, and an end seal 78. In addition, a protective coating 84 is formed around tube 74 and an end cap 86 covers end seal 78 and a portion of electrical lead 88. However, instead of ultraviolet lamp 72 having pins which plug directly into a base, power is provided directly to ultraviolet lamp 72 via electrical lead 88. In accordance with this particular aspect of the invention, the ballast portion of the ultraviolet light source (not shown) is separate from the ultraviolet light source 70. In addition, while the embodiment of FIG. 7 is shown as having a protective coating 84 and an end cap 86, one skilled in the art will appreciate that the two-piece design enables one to change lamp 72 easily. Thus, in accordance with an alternative embodiment, one solid protective coating may be used to cover lamp 72, and end seal 78. Therefore, the present invention is not limited to the illustrated embodiment.

Figure 8:
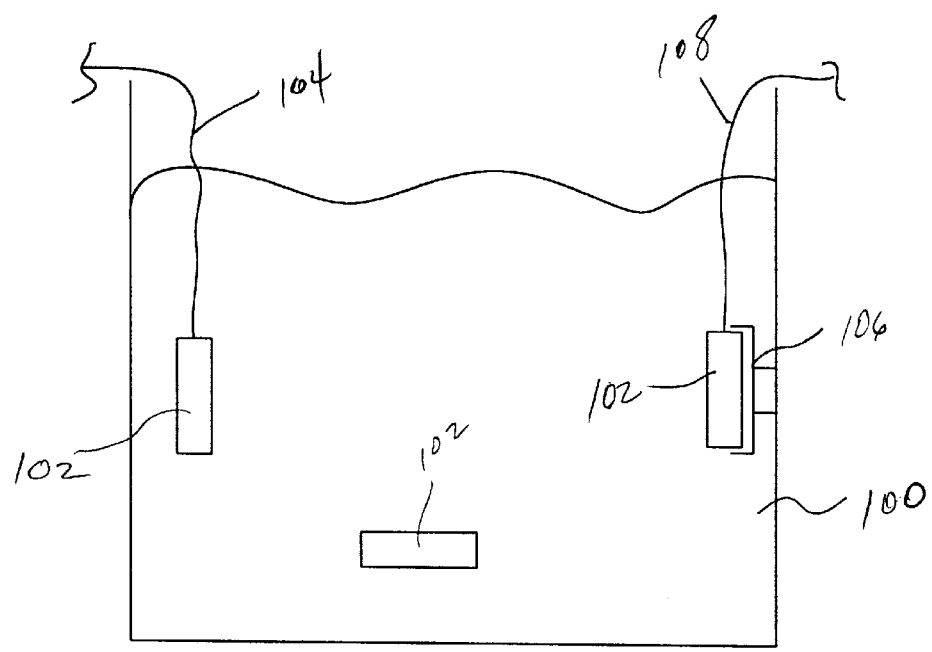
FIG. 8 is a side view drawing of a tank having a plurality of ultraviolet light sources mounted or deposited therein.

The ultraviolet light source of the present invention can be used for disinfecting and sterilizing fluids and fluid containers and handling equipment in a wide variety of different environments. The size and the configuration of the ultraviolet light source can be modified for use in various water or fluid tanks, as well as in air purification systems and handling equipment for fluids, including air and other gases. For example, as illustrated in FIG. 8, one of a variety of ultraviolet light source devices can be placed in a tank with water or other suitable fluid to help kill any organisms which might live within the tank. As illustrated in FIG. 8, an ultraviolet light source 102 may hang within tank 100 by a support line 104. In accordance with one embodiment of the present invention, support line 104 may be a lead wire or tether wire holding light source 102 in a preferred location. Alternatively, support line 104 also may act as an electrical lead line, providing electrical power to ultraviolet light source 102 via that means. Otherwise, in accordance with an alternative embodiment of the present invention, a battery pack, a solar power generator or other suitable power providing means may be used to provide power to light source 102. Similarly, an ultraviolet light source 102 may be secured in tank 100 by a clip 106 or other suitable securing device, and an electrical lead line 108 or a battery pack or the like, may be used. Finally, if ultraviolet light source 102 is powered by a battery pack or solar powered generator, the ultraviolet light source may be dropped into tank 100 without any supporting lines. In this manner ultraviolet light source 102 may drift to the bottom of tank 100, or it may be configured to float within the fluid tank.

Figure 9:
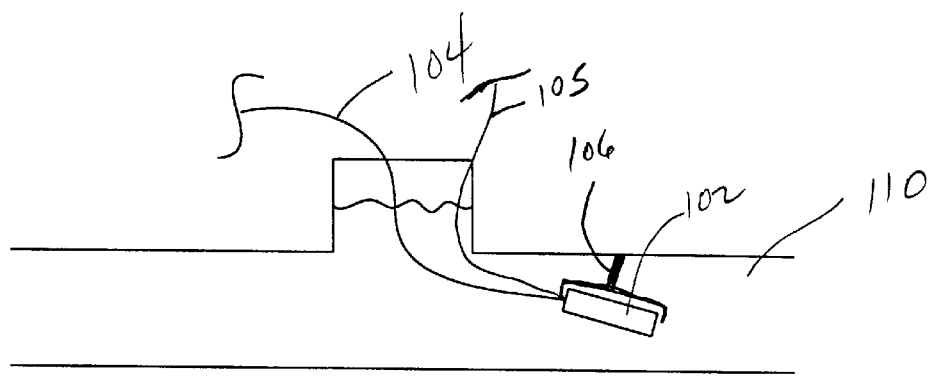
FIG. 9 is a side view drawing of a fluid carrying pipe having an ultraviolet light source deposited therein.

Referring now to FIG. 9, an alternative use of an ultraviolet light source 102 is illustrated. In this particular embodiment of the present invention, ultraviolet light source 102 is placed within a fluid pipe 110 which is configured to carry any number of different fluid types. Preferably, ultraviolet light source 102 is suspended within fluid pipe 110 using a support line 104. As with the embodiments illustrated in FIG. 8, support line 104 also may include an electrical lead connector for providing power to ultraviolet light source 102. In accordance with an alternative embodiment of the invention, light source 102 may include an electrical lead connector 104, as well as a separate lead wire 105. In this particular embodiment, the lead wire can be used to hold light source 102 in place, taking the pressure off electrical lead connector 104. Also, lead wire 105 can be used to move the light source 102 within the pipe 110. Finally, in accordance with yet another embodiment of the present invention, light source 102 may be mounted within fluid pipe 110 with, for example, a mounting bracket or clip 106.

Figure 10:
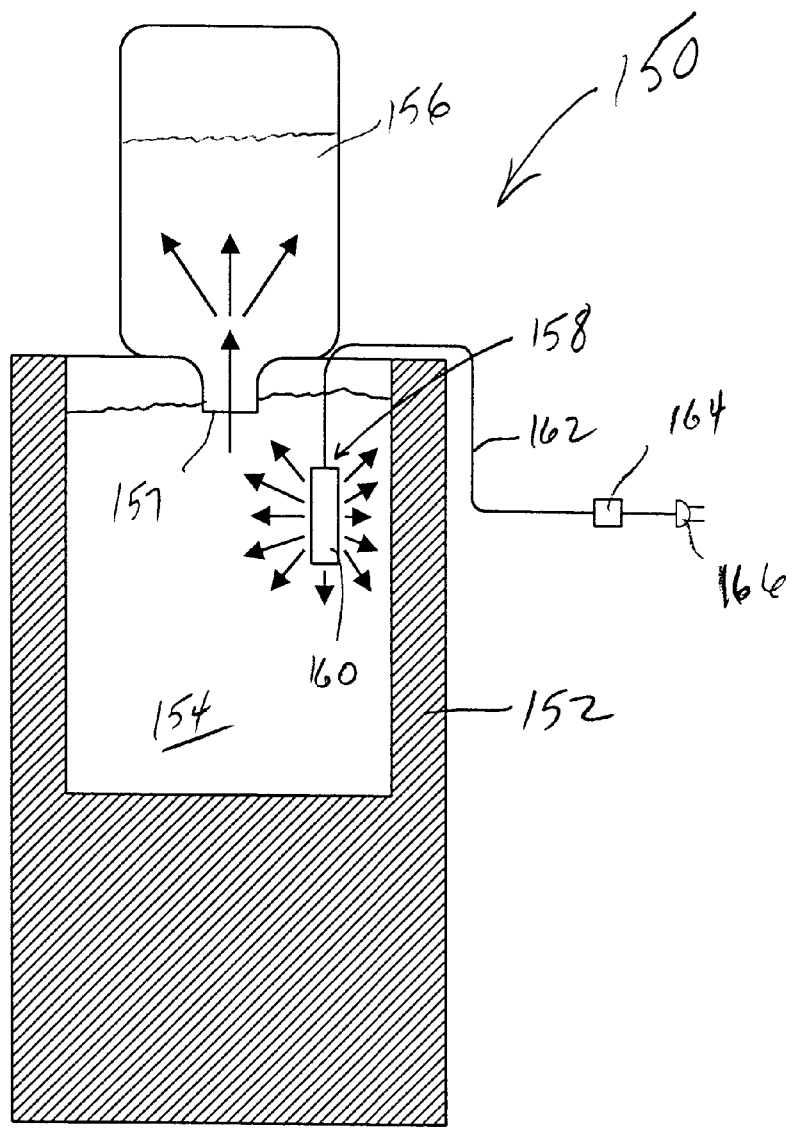
FIG. 10 is a side cross-sectional view of a water dispenser having an ultraviolet light source therein.

Referring now to FIG. 10, a use of an ultraviolet source in a drinking water dispenser 150 is shown. In accordance with this particular embodiment of the present invention, drinking water dispenser 150 preferably includes a base 152 having a water reservoir 154 therein, and a water bottle 156 provided in an inverted position on top of base 152 directly above reservoir 154. As one skilled in the art will appreciate, as water in reservoir 154 lowers below opening 157 in water bottle 156, water from water bottle 156 will pour into reservoir 154. In this manner, the water level in reservoir 154 is maintained.

In accordance with this particular embodiment of the present invention, an ultraviolet light source 158 preferably is placed in reservoir 154 of drinking water dispenser 150. Ultraviolet light source 158 preferably includes a light bulb 160, an electrical connector 162 for providing power to the light source. In addition, in accordance with the illustrated embodiment, light source 158 also may include an external ballast 164, and an AC plug adapter 166. When ultraviolet light source 158 is turned on, the UVC light emitted from the light source kills all the microorganisms that may be living in the water within reservoir 154 or on the sides of reservoir 154. In addition, the ultraviolet light source also may pass through opening 157 in water bottle 156, killing any microorganisms that may be living in water bottle 156. In this manner, the ultraviolet light 158 can be used to sterilize reservoir 154, the water within reservoir 154, water bottle 156, and the water within water bottle 156. Thus, the ultraviolet light source can be used as a safe and effective means to maintain a clean water environment. In addition, as mentioned above, because ultraviolet light source 158 and, in particular light bulb 160 of light source 158 preferably is enclosed in a protective coating, a corrosive film from algae and other organisms will not form on light bulb 160. In addition, if by chance light bulb 160 happens to break, the protective coating surrounding light bulb 160 will contain the broken glass and other materials from the light bulb, preventing those materials from being exposed to the water. In this manner, the water within reservoir 154 and water tank 156 will not be exposed to any harmful materials from lamp 160.

While only a few uses of ultraviolet light source 102 are illustrated in the drawings and disclosed herein, one skilled in the art will appreciate that an ultraviolet light source of the present invention may be used in any environment in which it is desirable to kill micro-organisms such as bacteria, molds, viruses, etc. For example, ultraviolet light source 102 can be used in conjunction with air conditioning devices and other air purification systems to kill the bacteria and molds that live within the air. Similarly, ultraviolet light source 102 can be used in a wide range of water tanks such as bottled water dispensers, RV and boat water tanks, cruise ships, livestock water tanks, and any other suitable fluid environment. In addition, by configuring an ultraviolet light source 102 into a small, compact package, the ultraviolet source can be placed in a glass of drinking water or a pitcher of drinking water to kill any organisms that are living within that immediate glass or pitcher. In this particular embodiment, the ultraviolet light source preferably is a self-contained, battery powered light source.

In conclusion, the present invention provides methods and apparatus for disinfecting and/or sterilizing fluids in a variety of fluid environments. While a detailed description of presently preferred embodiments of the invention have been given above, various alternatives, modifications, and equivalents will be apparent to those skilled in the art. For example, while various ultraviolet lamp configurations are disclosed herein, any number of different lamp configurations may be used without varying from the spirit of the invention. In addition, while various protective sleeves and coatings are disclosed, any shape and configuration of a protective sleeve or coating may be used. Therefore, the above description should not be taken as limiting the scope of the invention which is defined by the appended claims.

What is claimed is:

1. An ultraviolet light source, comprising:
   an ultraviolet lamp;
   said ultraviolet lamp comprising a protective coating surrounding and in touching proximity with said ultraviolet lamp, said protective coating hermetically sealing said ultraviolet lamp, and said protective coating having properties that allow the germicidal energy to pass; and
   a power source for providing power to said ultraviolet lamp.

2. The ultraviolet light source as recited in claim 1, wherein said ultraviolet lamp comprises a casing for holding a gas and a vaporizable material, and at least one electrode electrically coupled to said power source for exciting said gas and said vaporizable material.

3. The ultraviolet light source as recited in claim 1, wherein said protective coating a fluoropolymer material.

4. The ultraviolet light source as recited in claim 2, wherein said casing comprises a quartz or glass casing and said protective coating surrounding and in touching proximity with said quartz or glass casing.

5. The ultraviolet light source as recited in claim 3, wherein said fluoropolymer material comprises a fluoropolymer selected from the group of PTFE, FEP, PFA, AF, and Tefzel ETFE.

6. The ultraviolet light source as recited in claim 1, wherein said protective coating comprises a silicon polymer or silicone material.

7. The ultraviolet light source as recited in claim 4, wherein said protective coating protects said quartz or glass casing of said ultraviolet lamp from breaking.

8. The ultraviolet light source as recited in claim 4, wherein said protective coating is heat shrunk around said quartz or glass casing of said ultraviolet lamp.

9. The ultraviolet light source as recited in claim 4, wherein said protective coating is form pressed around said quartz or glass casing of said ultraviolet lamp.

10. The ultraviolet light source as recited in claim 3, wherein said fluoropolymer material is formed around said quartz or glass casing of said ultraviolet lamp by dipping said ultraviolet lamp into a liquid material.

11. The ultraviolet light source as recited in claim 1, wherein said protective coating thermally insulates said ultraviolet lamp.

12. The ultraviolet light source as recited in claim 1, wherein said power source is a solar power source connected to said ultraviolet lamp, and wherein said protective coating surrounds said solar power source and said ultraviolet lamp and hermetically seals said solar power source with said ultraviolet lamp.

13. The ultraviolet light source as recited in claim 1, wherein said ultraviolet lamp comprises a first end portion, a second end portion, and an elongated body portion formed between said first end portion and said second end portion, and wherein said protective coating comprises a fluoropolymer material covering at least part of said elongated body portion, and first and second end caps covering at least a part of said first and said second end portions, respectively, said first and said second end caps forming a seal with said fluoropolymer material.

14. The ultraviolet light source as recited in claim 13, wherein said first and said second end caps comprise fluoropolymer end caps.

15. The ultraviolet light source as recited in claim 13, wherein said first and said second end caps comprise silicone end caps.

16. The ultraviolet light source as recited in claim 13, wherein said first and said second end caps are sealed to said protective coating using a silicone sealer.

17. The ultraviolet light source as recited in claim 1, wherein said ultraviolet light source is operable to kill microorganisms in fluids.

18. The ultraviolet light source as recited in claim 1, wherein said power source comprises an electrical connector connecting said power source to said ultraviolet lamp, and wherein said protective coating forms a seal with said electrical connector.

19. The ultraviolet light source as recited in claim 13, wherein said power source comprises an electrical connector connecting said power source to said ultraviolet lamp, and wherein one or both of said first and said second end caps form a seal with said electrical connector.

20. The ultraviolet light source as recited in claim 19, wherein said first end portion includes a first electrode, and said second end portion includes a second electrode, and wherein said electrical connector provides power to said first and said second electrodes, said electrical connector comprising one or more electrically transmissive wires running the length of said body portion and connecting said second electrode at the second end portion to said power source, said first end cap forming a seal with said electrical connector, and said fluoropolymer material covering at least a portion of said one or more electrically transmissive wires.

21. An ultraviolet light source, comprising:
   an ultraviolet lamp comprising a first end portion, a second end portion and a body portion formed between said first and said second end portions, said first end portion including a first electrode, and said second end portion including a second electrode;
   a power source for providing power to said ultraviolet lamp, said power source comprising an electrical connector for providing power to said first and said second electrodes, said electrical connector comprising one or more electrically transmissive wires running the length of said body portion and connecting said second electrode at the second end portion to said power source;
   a protective coating surrounding and in touching proximity with said ultraviolet lamp, said protective coating hermetically sealing said ultraviolet lamp and said one or more electrically transmissive wires running the length of said body portion.

22. The ultraviolet light source as recited in claim 21, wherein said protective coating forms a seal with said electrical connector.

23. The ultraviolet light source as recited in claim 21, wherein said protective coating comprises a fluoropolymer material.

24. The ultraviolet light source as recited in claim 23, wherein said fluoropolymer material comprises a fluoropolymer selected from the group of PTFE, FEP, PFA, AF, and Tefzel ETFE.

25. The ultraviolet light source as recited in claim 21, wherein said protective coating comprises a fluoropolymer material covering at least part of said body portion, and first and second end caps covering at least part of said first and said second end portions, respectively, said first and said second end caps forming a seal with said fluoropolymer material.

26. The ultraviolet light source as recited in claim 25, wherein said first end cap forms a seal with said electrical connector.

27. An ultraviolet light source, comprising:

a power source, and an ultraviolet lamp, comprising a casing and at least one base electrically coupled to said power source for causing the ultraviolet lamp to emit light, at least said casing being substantially surrounded by a fluoropolymer material, which is touching said casing, and at least a portion of said at least one base being covered by an end cap, said end cap forming a seal with said fluoropolymer material.

28. The ultraviolet light source as recited in claim 27, wherein said power source is electrically coupled to said at least one electrode by an electrical connector, and wherein said end cap forms a seal with said electrical connector.

29. An ultraviolet light source, comprising:

an ultraviolet lamp and a power source for providing power to said ultraviolet lamp, said power source for causing said ultraviolet lamp to emit ultraviolet light, the entirety of said ultraviolet lamp being coated by a fluoropolymer material, which is in touching proximity to said ultraviolet lamp, such that said ultraviolet lamp is hermetically sealed by said fluoropolymer material.

30. The ultraviolet light source as recited in claim 29, wherein said fluoropolymer material comprises a fluoropolymer selected from the group of PTFE, FEP, PFA, AF and Tefzel ETFE.

31. The ultraviolet light source as recited in claim 29, wherein said fluoropolymer material is heat shrunk around said ultraviolet lamp.

32. The ultraviolet light source as recited in claim 29, wherein said fluoropolymer material is formed around said ultraviolet lamp by dipping said ultraviolet lamp into a fluoropolymer liquid material.

* * * * *